(12) United States Patent
Gollwitzer et al.

(10) Patent No.: US 11,278,265 B2
(45) Date of Patent: Mar. 22, 2022

(54) INTEGRATABLE BIOPSY UNIT AND MAMMOGRAPHY DEVICE

(71) Applicant: Siemens Healthcare GmbH, Erlangen (DE)

(72) Inventors: Helmut Gollwitzer, Erbendorf (DE); Wolfgang Neuber, Pressath (DE); Juliane Ritter, Erlangen (DE); Mario Bechtold, Hemhofen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 529 days.

(21) Appl. No.: 16/254,670

(22) Filed: Jan. 23, 2019

(65) Prior Publication Data

US 2019/0231323 A1 Aug. 1, 2019

(30) Foreign Application Priority Data

Jan. 30, 2018 (EP) .................................... 18154188

(51) Int. Cl.
| | |
|---|---|
| *A61B 6/04* | (2006.01) |
| *A61B 10/02* | (2006.01) |
| *A61B 6/00* | (2006.01) |
| *A61B 90/17* | (2016.01) |
| *A61B 90/11* | (2016.01) |

(52) U.S. Cl.
CPC ............ *A61B 10/0233* (2013.01); *A61B 6/04* (2013.01); *A61B 6/502* (2013.01); *A61B 90/11* (2016.02); *A61B 90/17* (2016.02); *A61B 6/0414* (2013.01)

(58) Field of Classification Search
CPC ..... A61B 10/0233; A61B 6/04; A61B 6/0414; A61B 6/502; A61B 90/11; A61B 90/17
See application file for complete search history.

(56) References Cited

U.S. PATENT DOCUMENTS

2016/0296186 A1* 10/2016 Hugg ........................ A61B 6/12

FOREIGN PATENT DOCUMENTS

| DE | 102006004590 A1 | 8/2007 |
|---|---|---|
| DE | 102011081420 A1 | 8/2012 |
| WO | WO 2012032810 A1 | 3/2012 |

OTHER PUBLICATIONS

European Search Report EPA Form 1507N for European Application No. EP18154188 dated Jul. 18, 2018.

* cited by examiner

*Primary Examiner* — Mark D Remaly
(74) *Attorney, Agent, or Firm* — Harness, Dickey & Pierce, P.L.C.

(57) ABSTRACT

A biopsy unit is for fixing to a mammography device. In an embodiment, the biopsy unit includes a fixing device and a receptacle for a biopsy needle. The biopsy unit is permanently connectable to the mammography device, and wherein the biopsy unit is pivotable between a rest state and an operating state.

20 Claims, 5 Drawing Sheets

INTEGRATABLE BIOPSY UNIT AND MAMMOGRAPHY DEVICE

PRIORITY STATEMENT

The present application hereby claims priority under 35 U.S.C. § 119 to European patent application number EP 18154188.9 filed Jan. 30, 2018, the entire contents of which are hereby incorporated herein by reference.

FIELD

Embodiments of the invention generally relate to a biopsy unit and a mammography device with a biopsy unit integrated therein.

BACKGROUND

To perform biopsies during a mammography, mammography devices are known onto which a biopsy unit can be placed. Such a biopsy unit comprises in particular a receptacle for a biopsy needle, a means for moving the receptacle between a first and at least one predetermined second position, and a control unit for controlling the movement means and for predetermining the second position.

Known mammography devices comprise a main body, which extends for example in a vertical direction, an image acquisition device and a compression unit. The image acquisition device and/or the compression unit are rigidly or pivotably connected to the main body. To this end the image acquisition device and compression unit can be arranged on a pivotable arm connected to the main body. Biopsy units for such mammography devices are known which are connected to the mammography device for the performance of a biopsy.

In a known device the biopsy unit can be placed on a support table of the compression unit. The biopsy unit must be readjusted each time it is used, so that the biopsy can be performed at the intended position. Moreover, for the use of such a biopsy unit it is necessary for a compression element of the compression unit to be provided with a special frame which can surround the biopsy unit.

Another known biopsy unit is embodied as a fixture for a further mammography device. The biopsy unit is accommodated in two vertical guide grooves of the main body of the mammography device. With this known biopsy unit too, it is necessary to readjust the biopsy unit prior to each usage.

SUMMARY

At least one embodiment of the invention is directed to reducing or eliminating the disadvantages according to the prior art. In particular, in embodiments, a biopsy unit and a mammography device are specified that have increased operating convenience for the performance of a biopsy.

Embodiments are directed to a biopsy unit and a mammography device. Advantageous embodiments of the invention are the subject matter of the claims.

At least one embodiment of the invention is directed to biopsy unit for fixing to a mammography device, comprising
 a fixing device,
 a receptacle for a biopsy needle,
 wherein the biopsy unit is permanently connectable to the mammography device, and is pivotable between a rest state and an operating state.

At least one embodiment of an inventive mammography device comprises:
 a main body which in particular extends in a vertical direction,
 an image acquisition device,
 a compression unit, and
 at least one embodiment of the inventive biopsy unit.

The above-described properties, features and advantages of this invention and the manner in which these are achieved will be described more clearly and explicitly with the following description of the exemplary embodiments, which are explained in more detail with the drawings.

BRIEF DESCRIPTION OF THE DRAWINGS

For a further description of the invention, reference is made to the exemplary embodiments of the drawings. These are schematic principle sketches in which.

DETAILED DESCRIPTION OF THE EXAMPLE EMBODIMENTS

Figure 1:
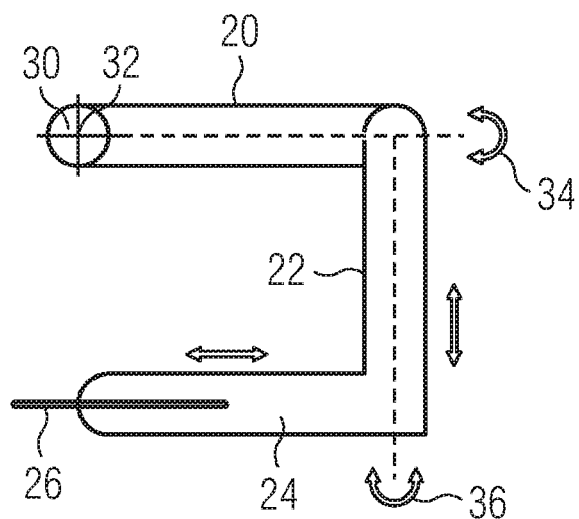
FIG. 1 shows a biopsy unit in the rest state

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the invention is directed to biopsy unit for fixing to a mammography device, comprising
a fixing device,
a receptacle for a biopsy needle,
wherein the biopsy unit is permanently connectable to the mammography device, and is pivotable between a rest state and an operating state.

In the operating state the biopsy unit is positioned such that a biopsy can be performed with the biopsy unit. In the rest state it is not possible to perform a biopsy with the biopsy unit.

In one embodiment, the biopsy unit comprises a first arm which on the fixing device can move about a first axis, and a second arm which can move about a second axis.

The first axis can be a horizontal axis and/or the second axis can run parallel to the first arm.

In one embodiment, the second arm is connected to a third arm on the side facing away from the first arm, the third arm being in particular at an angle of between 90° and 100° to the second arm and/or being movable about a third axis running parallel to the second arm. The angle between the second and third arm can be permanently selected in the angular range or can be adjustable.

The first arm, the second arm and/or the third arm can be configured so as to be adjustable in terms of length. Thus the flexibility of the biopsy device is increased.

The third arm expediently runs substantially parallel to the first arm in an operating position.

In one embodiment the receptacle for a biopsy needle is arranged on the third arm.

At least one embodiment of an inventive mammography device comprises:
a main body which in particular extends in a vertical direction,
an image acquisition device,
a compression unit, and
at least one embodiment of the inventive biopsy unit.

The biopsy unit can if required simply be swung out and need not first be connected to the mammography device prior to each use and subsequently adjusted. An adjustment of the mammography device is preserved even when it is pivoted into the rest state.

The mammography device expediently has a housing which is configured such that the biopsy unit is accommodated in the housing in the rest state. The housing can in particular be an annular housing. At least one opening is expediently provided on an outer ring surface, such that the biopsy unit can be partially pivoted out of the housing when pivoted from the rest state to the operating state. The opening can be movable on the outer ring surface.

In a further embodiment, the device has a single control device for controlling the image acquisition and for controlling the biopsy unit or has intercommunicating control devices for controlling the image acquisition device and for controlling the biopsy unit. By providing a shared control device or intercommunicating control devices the use of the mammography device with the biopsy unit is facilitated.

FIG. 1 shows the biopsy unit 10 in a rest state. A first arm 20 can also be rotated on the fixing device 30 about a horizontal first axis 32. In the example the first arm 20 is configured so that it can be adjusted in length. Extending from the first arm 20 is a second arm 22 which likewise is configured so that it can be adjusted in length, and extending from the second arm 22 is a third arm 24 which can also be adjusted in length. The second arm 22 can move about a second axis 34 which is aligned parallel to the first arm 20. The third arm 24 can move about a third axis 36 which runs parallel to the second arm 22. The third arm 24 serves to accommodate a biopsy needle 26.

Figure 2:
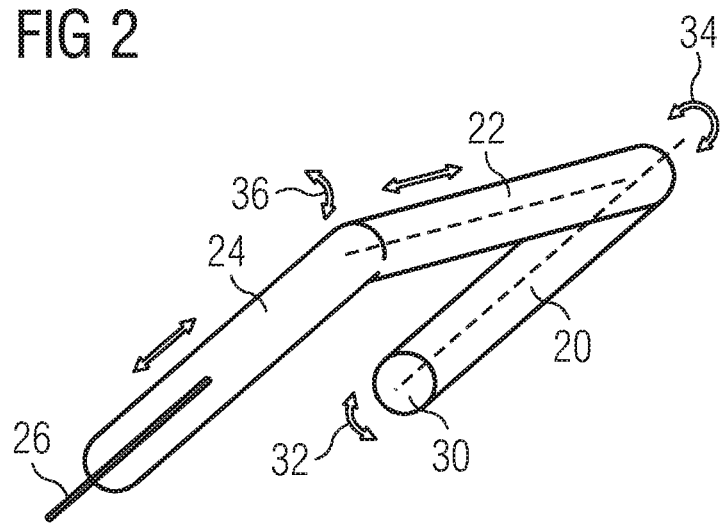
FIG. 2 shows a biopsy unit in the operating state

In the operating state shown in FIG. 2 the second arm 22 is pivoted about the axis extending parallel to the first arm 20. By rotating the biopsy unit 10 about the first axis 32 and the second axis 34 running parallel to the first arm 20 and the third axis 36 a biopsy can be performed at the desired position of the object using the biopsy unit 10.

Figure 3:
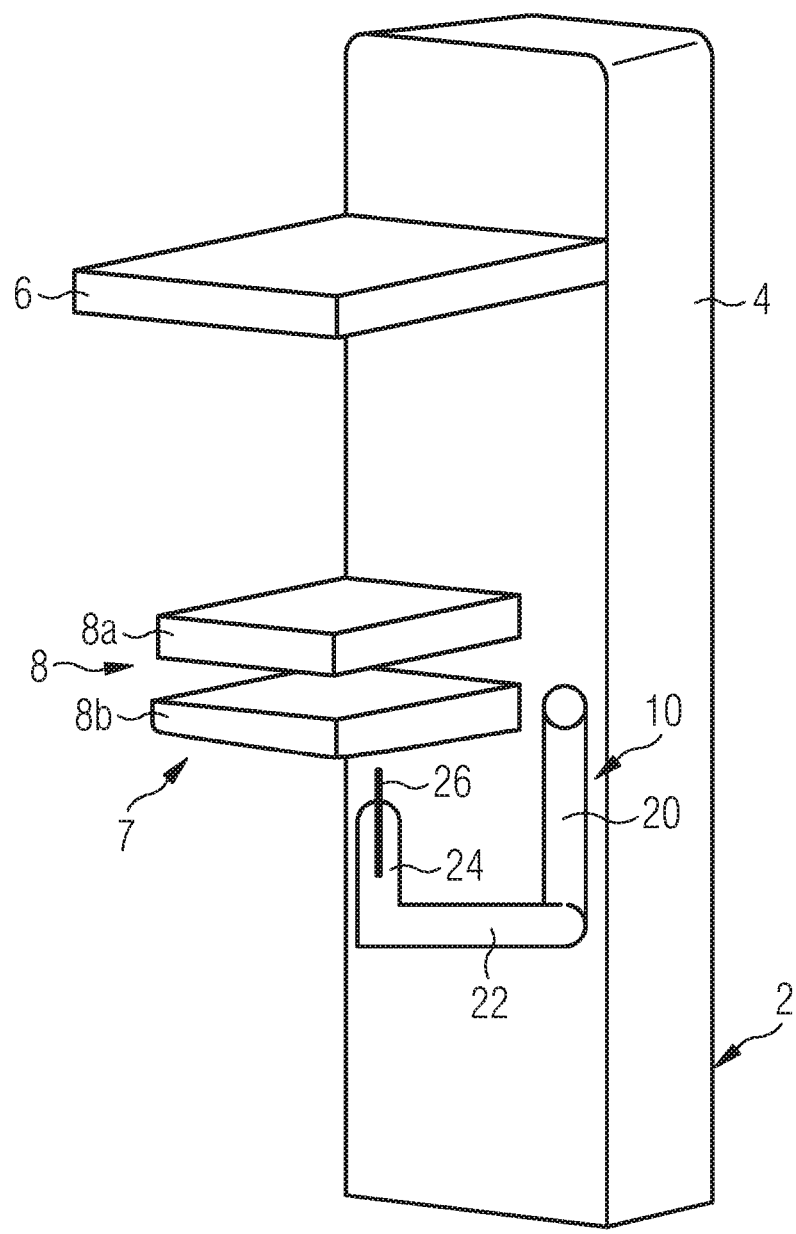
FIG. 3 shows a first embodiment of the inventive mammography device with biopsy unit in the rest state

FIG. 3 shows a first embodiment of an inventive mammography device 2. The mammography device 2 comprises a main body 4 which extends in a vertical direction. A main body 4 can also extend horizontally in another embodiment. An X-ray source 6 is arranged in the upper region of the main body 4 on a cross-arm, and with the detector forms the image acquisition device. Attached to the main body 4 is the biopsy device 10, which is in the rest state.

Figure 4:
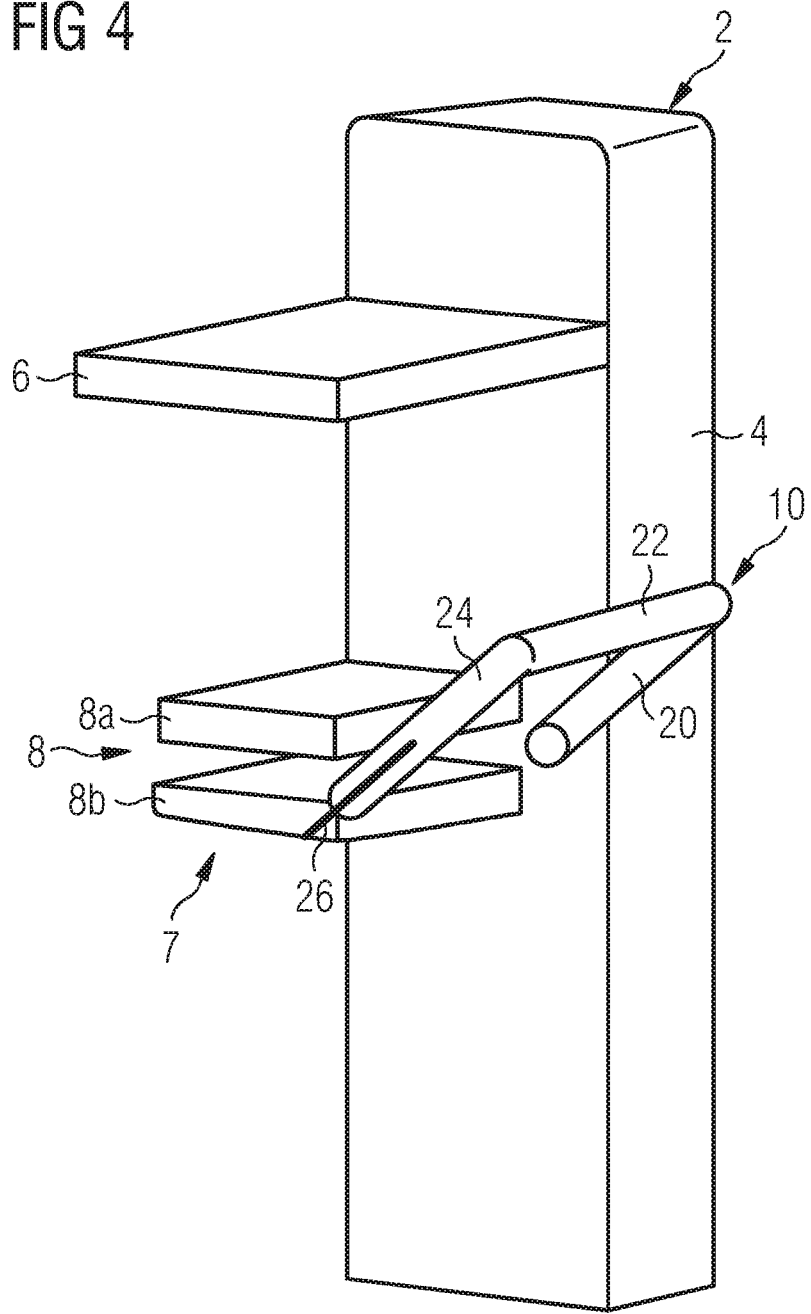
FIG. 4 shows a first embodiment of the inventive mammography device with biopsy unit in the operating state

FIG. 4 shows the embodiment of the invention shown in FIG. 3 with the biopsy unit 10 in the operating state. The biopsy unit 10 is pivoted away from the main body 4, such that the second arm 22 extends perpendicular to the direction of extension of the main body 4. A third arm 24 extends substantially perpendicular to the second arm 22 and serves to accommodate a biopsy needle 26.

Figure 5:
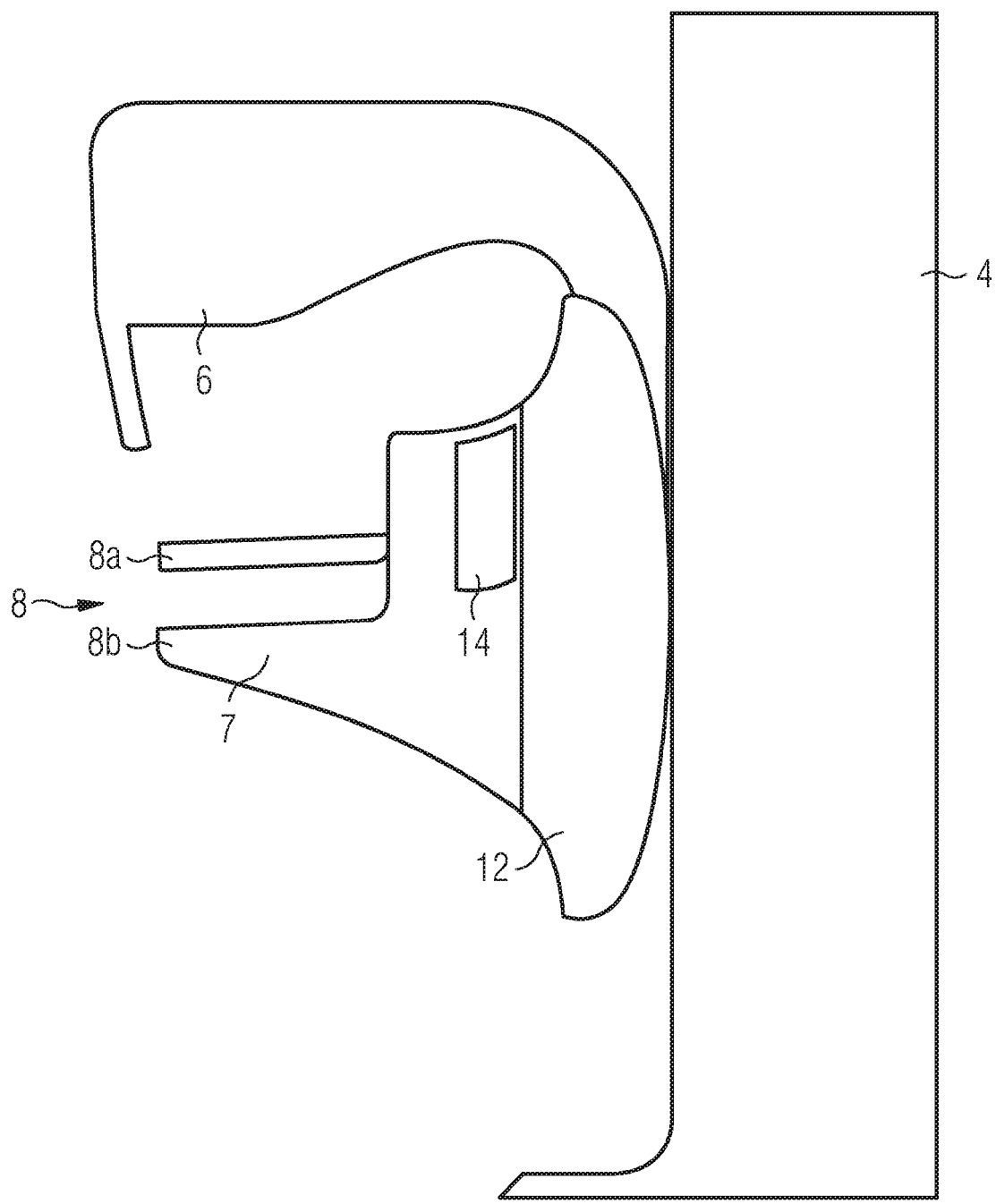
FIG. 5 shows a second embodiment of the inventive mammography device with biopsy unit in the rest state
Figure 6:
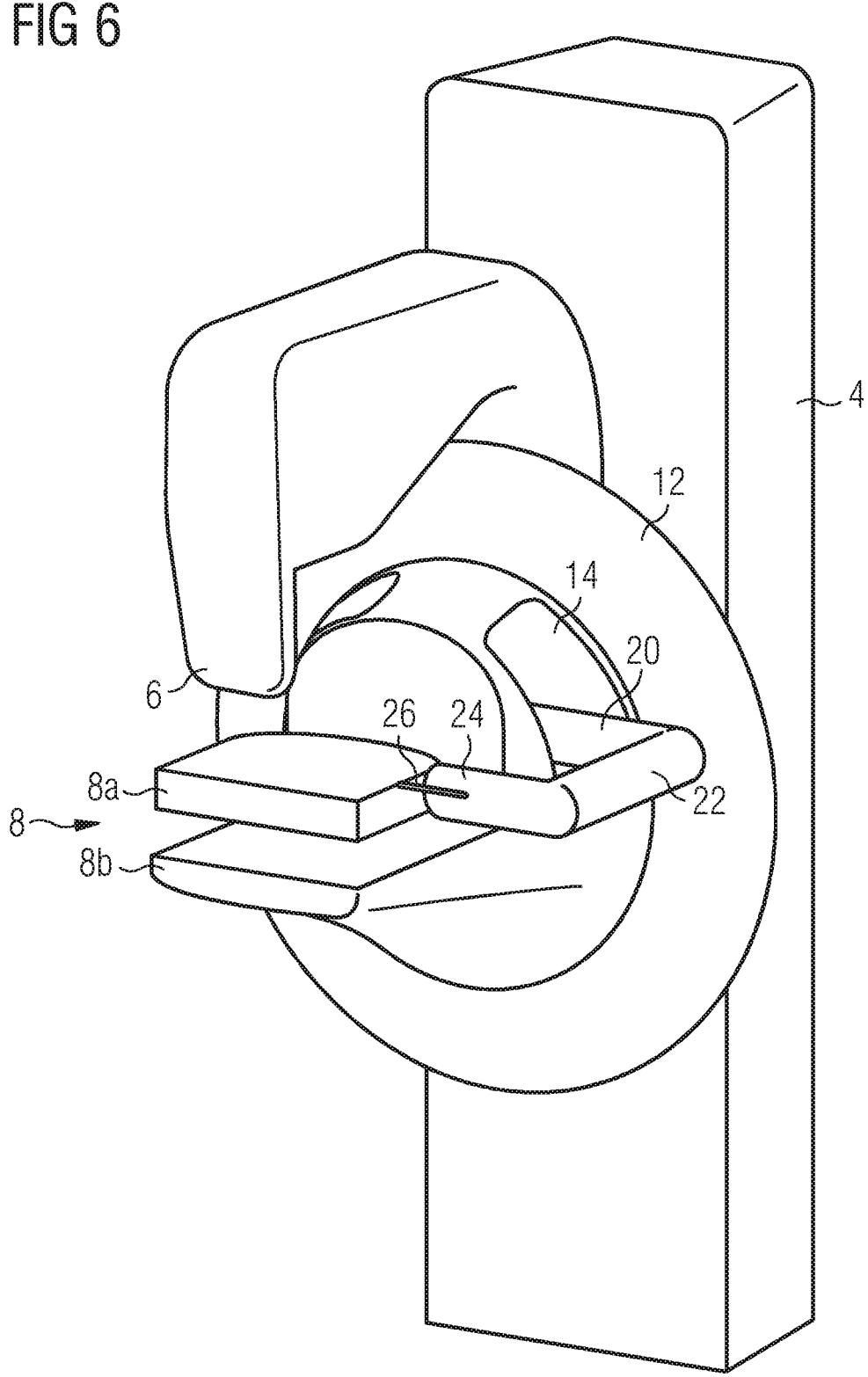
FIG. 6 shows a second embodiment of the inventive mammography device with biopsy unit in the operating state

FIGS. 5 and 6 show a second embodiment of the inventive mammography device 2. The second embodiment additionally has a housing 12 with at least one opening 14. The housing 12 is connected to the main body 4. On the side of the housing 12 facing away from the main body 4 the compression unit consisting of compression element 8a and object table 8b is arranged such that using the X-ray source 6 an object located in the compression unit 8 can be X-rayed. The radiation is recorded using a detector 7 located in the region of the object table 8b. In FIG. 5 the biopsy unit 10 is in the rest state and fully accommodated in the housing 12. In FIG. 6 the biopsy unit 10 is in the operating state and partially protrudes out of an opening 14 in the housing. The opening 14 can be larger than shown, so that for example it permits a pivoting movement of ±90° about the first axis 32, or can be moved in the housing 12 in order to permit a corresponding pivoting movement. The first arm 20 is partially outside the housing 12 while the second arm 22 and the third arm 24 are completely outside the housing 12.

Although the invention has been illustrated and described in detail with the preferred exemplary embodiment, the invention is not restricted by the examples given and other variations can be derived therefrom by a person skilled in the art without departing from the protective scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A biopsy unit for fixing to a mammography device, comprising:
   an articulated arm having at least a first arm segment and a second arm segment, the second arm segment extending from the first arm segment;
   a fixing device at a first end of the articulated arm; and
   a receptacle for a biopsy needle, wherein
      the biopsy unit is permanently connectable to the mammography device, and wherein the biopsy unit is pivotable between a rest state and an operating state.

2. The biopsy unit of claim 1, wherein
   the first arm segment, being rotatable on the fixing device on a first axis; and
   the second arm segment being movable about the first arm on a second axis.

3. The biopsy unit of claim 2, wherein at least one of
   the first axis is a horizontal axis and
   the second axis runs parallel to the first arm segment.

4. The biopsy unit of claim 2, wherein the articulated arm has a third arm segment connected to the second arm segment on a side facing away from the first arm segment.

5. The biopsy unit of claim 2, wherein the first arm segment is adjustable in terms of length.

6. The biopsy unit of claim 4, wherein the third arm segment runs substantially perpendicular to the second arm segment in an operating position.

7. The biopsy unit of claim 4, wherein the receptacle for a biopsy needle is arranged on the third arm segment.

8. A mammography device, comprising:
   a main body, extending in a vertical direction;
   an imager;
   a compression plate; and
   the biopsy unit of claim 1.

9. The mammography device of claim 8, further comprising:
   a housing, wherein the biopsy unit if fully accommodated within the housing in the rest state.

10. The mammography device of claim 8, further comprising:
    a single to controller to control the imager and to control the biopsy unit; or
    intercommunicating controllers to control the imager and to control the biopsy unit.

11. The biopsy unit of claim 4, wherein the third arm segment is s at least one of
    at an angle of between 90° and 100° to the second arm segment, and
    movable about a third axis running parallel to the second arm segment.

12. The biopsy unit of claim 3, wherein the second arm segment is connected to a third arm segment on a side facing away from the first arm segment.

13. The biopsy unit of claim 12, wherein the third arm segment is at least one of
    at an angle of between 90° and 100° to the second arm segment, and
    movable about a third axis running parallel to the second arm segment.

14. The biopsy unit of claim 2, wherein at least one of the first arm segment and the second arm segment is adjustable in terms of length.

15. The biopsy unit of claim 12, wherein at least one of the first arm segment, the second arm segment and the third arm segment is adjustable in terms of length.

16. The biopsy unit of claim 12, wherein the third arm segment runs substantially perpendicular to the second arm segment in an operating position.

17. The biopsy unit of claim 13, wherein the third arm segment runs substantially perpendicular to the second arm segment in an operating position.

18. The biopsy unit of claim 6, wherein the receptacle for a biopsy needle is arranged on the third arm segment.

19. A mammography device, comprising:
    a main body, extending in a vertical direction;
    an imager;
    a compression plate; and
    the biopsy unit of claim 2.

20. A mammography device, comprising:
    a main body, extending in a vertical direction;
    an imager;
    a compression plate; and
    the biopsy unit of claim 4.

* * * * *